(12) United States Patent
Shimokita (10) Patent No.: US 8,790,333 B2
(45) Date of Patent: Jul. 29, 2014

(54) SKULL CUTTING DEVICE

(75) Inventor: Ryo Shimokita, Hamamatsu (JP)

(73) Assignee: The Graduate for the Creation of New Photonics Industries, Hamamatsu-shi (JP)

(*) Notice: Subject to any disclaimer, the term of this patent is extended or adjusted under 35 U.S.C. 154(b) by 114 days.

(21) Appl. No.: 12/527,761

(22) PCT Filed: Feb. 19, 2007

(86) PCT No.: PCT/JP2007/052993
§ 371 (c)(1),
(2), (4) Date: Aug. 19, 2009

(87) PCT Pub. No.: WO2008/102428
PCT Pub. Date: Aug. 28, 2008

(65) Prior Publication Data
US 2010/0049183 A1 Feb. 25, 2010

(51) Int. Cl.
*A61B 18/20* (2006.01)
*A61B 17/00* (2006.01)
*A61B 17/16* (2006.01)
*A61B 18/22* (2006.01)

(52) U.S. Cl.
CPC ..... *A61B 17/1695* (2013.01); *A61B 2018/2272* (2013.01)
USPC ............................................. 606/17; 606/79

(58) Field of Classification Search
CPC ................. A61B 17/1695; A61B 2018/00005; A61B 18/203; A61B 18/201; A61B 2018/2272
USPC .......... 600/451; 606/2–19, 39, 167–173, 182; 607/88–89
See application file for complete search history.

(56) References Cited

U.S. PATENT DOCUMENTS 3,858,577 A * 1/1975 Bass et al. ...................... 600/108
4,979,180 A * 12/1990 Muncheryan .................... 372/92
(Continued)

FOREIGN PATENT DOCUMENTS

JP 1981104653 A 8/1981
JP 05-154208 6/1993
(Continued)

OTHER PUBLICATIONS

Fried et al., "Comparison of Er:YAG and 9.6-Im TE CO2 Lasers for Ablation of Skull Tissue", Lasers in Surgery and Medicine 28:335-343 (2001).*
(Continued)

*Primary Examiner* — Gary Jackson
*Assistant Examiner* — Scott T Luan
(74) *Attorney, Agent, or Firm* — Allenman Hall McCoy Russell & Tuttle LLP (57) ABSTRACT

A skull cutting device for cutting a skull by means of laser comprises a body for emitting the laser introduced from a laser oscillator through an optical fiber from an exit opening arranged at a distal end thereof, a contact portion arranged in the body to determine the posture of the body such that a predetermined distance is set between a surface of the skull and the exit opening by touching the surface of the skull in a predetermined mode, a support bar of a predetermined length extending from the body toward the emitting direction of the laser while avoiding the optical path of the laser (R), and a light interception board arranged at a distal end of the support bar to block farther advance of the laser by interfering with the laser beam path.

9 Claims, 6 Drawing Sheets

(56) References Cited

U.S. PATENT DOCUMENTS

| | | | |
|---|---|---|---|
| 5,250,065 A * | 10/1993 | Clement et al. | 606/172 |
| 5,304,191 A * | 4/1994 | Gosselin | 606/172 |
| 5,586,981 A * | 12/1996 | Hu | 606/9 |
| 5,628,748 A * | 5/1997 | Vicari | 606/79 |
| 5,836,939 A * | 11/1998 | Negus et al. | 606/11 |
| 6,001,115 A * | 12/1999 | Ahola et al. | 606/176 |
| 6,226,554 B1 * | 5/2001 | Tu et al. | 607/122 |
| 6,451,010 B1 * | 9/2002 | Angeley | 606/17 |
| 6,506,199 B2 * | 1/2003 | Rogers et al. | 606/172 |
| 2004/0054366 A1 * | 3/2004 | Davison et al. | 606/39 |
| 2005/0259933 A1 * | 11/2005 | Temelkuran et al. | 385/123 |
| 2006/0020309 A1 * | 1/2006 | Altshuler et al. | 607/88 |
| 2007/0100330 A1 * | 5/2007 | Tilleman | 606/17 |
| 2008/0186591 A1 * | 8/2008 | Altshuler et al. | 359/703 |
| 2008/0294187 A1 * | 11/2008 | Krisht | 606/192 |

FOREIGN PATENT DOCUMENTS

| | | |
|---|---|---|
| JP | 07-047081 | 2/1995 |
| JP | 2002-238911 | 8/2002 |
| JP | 3544548 | 7/2004 |
| JP | 2005-118325 | 5/2005 |
| WO | 89/11834 | 12/1989 |

OTHER PUBLICATIONS

Fried et al. ("Dental Hard Tissue Modification and Removal using Sealed TEA Lasers Operating at $\lambda=9.6$ and $\lambda=10.6$ μm," Proceedings of SPIE, vol. 3593 (1) SPIE, May 19, 1999).*

Fried et al. ("Comparison of Er:YAG and 9.6-Im TE CO2 Lasers for Ablation of Skull Tissue", Lasers in Surgery and Medicine 28:335-343 (2001)).*

ISA/Japanese Patent Office, International Search Report of PCT/JP2007/052993, May 15, 2007, 2 pages, Japan.

* cited by examiner

SKULL CUTTING DEVICE

FIELD OF THE ART

This invention relates to a skull cutting device that is preferably used for an operation on a brain of a human or an animal.

BACKGROUND ART

It is necessary to conduct craniotomy by removing a necessary portion of a skull after incising a scalp in a case of operating a damaged portion in a brain. A range to conduct the craniotomy depends on a disorder and a portion where a tumor exists due to a brain tumor.

There are several kinds of methods as shown in patent document 1 as a representative method for conducting the craniotomy. For example, one of the methods is to perforate several relatively big holes (burr holes) along a range of the skull where the craniotomy is to be conducted by the use of a perforator as being a drill configured for boring the skull and then to cut the skull along a line connecting these burr holes by the use of a rotary blade of a craniotome in a shape of an end mill head.

An automatic light interception mechanism is arranged to perforate the burr holes in the skull in order to avoid further reaching deeper of a distal end of the drill at a time when the distal end of the drill penetrates the skull. Then the rotary blade is inserted into the burr hole that has been perforated as mentioned above and the skull is cut along a rotary range that has been previously set. Hereinafter there is a case that a portion of the skull cut in the predetermined range is termed as a bone flap for simplification.

After the bone flap is removed and the damaged portion in the brain is operated on, the bone flap is to be returned to the cut portion so as to close the skull. In order to close the skull, the bone flap is fixed to the skull by screwing both the bone flap and the skull so as to not to cave in by means of a fixing member comprising a plate of titanium lying between the bone flap and its circumference of the skull.

In addition to the above, there is a method for cutting the skull called a wire saw craniotomy which is another method for craniotomy. This method is to cut the skull between the adjacent burr holes by the use of a metal jigsaw.

Furthermore, there is also another method called a trephine craniotomy to cut the skull in a circle with a circular saw by rotating its circular blade.

Patent document 1: Japan Patent Laid-open number 2002-238911

DISCLOSURE OF THE INVENTION

Problems to be Solved by the Invention

With either method, however, the head of the patient is required to be tightly fixed by the use of a dedicated fixing member because a mechanical jig such as a drill is used to conduct the craniotomy procedure. As a result, the patient is forced to bear a big burden although the patient is unconscious because of anesthesia.

In addition, since the skull is in a very much slippery state due to a body fluid such as a blood of the patient at a time of the craniotomy procedure and furthermore since it is not allowed to damage other tissue (especially brain) of the patient, a physical and mental burden for the operator becomes more than imagined in a case of boring or cutting the skull.

Furthermore, with a conventional method, since a cutting margin is big (for example, about 3 mm) so that the bone flap becomes small, there is a problem that the bone flap caves in at a time of returning the bone flap to the original position on the skull in order to close the skull because a big gap is generated between the bone flap and the skull. In order to solve this problem, presently both the bone flap and the skull are fixed by the use of the fixing member formed on the plate made of expensive titanium.

The present claimed invention focuses attention on a gap existing between the skull and the brain, and a main object of this invention is to provide a skull cutting device that can make it possible to conduct an operation safely and easily while lessening the burden for the patient in case of the craniotomy procedure.

Means to Solve the Problems

In order to solve the above problems, the present claimed invention takes the following measures.

More specifically, the skull cutting device in accordance with this invention is a skull cutting device for cutting a skull by means of laser and is characterized by comprising a body that emits the laser introduced from a laser oscillator through an optical fiber from an exit opening arranged at a distal end thereof, a contact portion arranged in the body to contact with or close to a surface of the skull, a support bar extending from the body toward the emitting direction of the laser while avoiding the optical path of the laser, and a light interception board that is supported at a distal end of the support bar and that blocks farther advance of the laser by interfering with the laser beam path by being inserted between a back surface of the skull and a surface of the brain in a state that the contact portion makes contact with or is close to the surface of the skull.

If the skull cutting device further comprises a detect device that detects whether or not the contact portion makes contact with or is close to the surface of the skull, it is possible to add several mechanisms to improve the safety such that the laser is automatically shut off by making use of the detect device, for example, at a time when the body is separated from the surface of the skull.

In order to prevent the bone flap from dropping inside the brain at a time of closing the skull by forming the bone flap in a cone shape (or an inverted cone shape), it is preferable that the detect device also detects whether or not an optical axis of the laser is generally orthogonal to the surface of the skull as being an area to which the laser is to be emitted and the operator relies on the detect device while cutting the skull. This is because if the spherical skull is cut with the cut surface generally orthogonal to the surface of the skull, the shape of the bone flap becomes an inverted cone shape by itself.

Since a thickness of the skull varies between individuals or depends on a cut portion, in order to cope with this variety it is preferable that the support bar is of varying-length.

In order to obtain the power that is necessary and sufficient to efficiently cut the bone, it is preferable that the skull cutting device further comprises an optical system arranged inside of the body, wherein the optical system comprises a circular polarizer that circularly polarizes at least the laser emitted from the optical fiber and a convex lens element that converges the laser.

In order to both secure the safety and check the point on the skull emitted by the laser with eyes so as to make it possible to cut more accurately, it is preferable that a photic area made of a translucent material having a light diffusion action is arranged near the exit opening of the body.

In order to make it possible to protect the optical system from a body fluid or a bone fragment splashing at a time of cutting and to easily wash away the body fluid or the bone fragment, it is preferable that the body comprises a main body, a head portion detachably arranged at a distal end of the main body and a transparent antiscattering plate having an equal thickness that is arranged orthogonal to the optical axis of the laser and that divides an inside space of the head portion.

In order to make it possible to move the body smoothly with keeping the optical axis of the laser orthogonal to the surface of the skull, it is preferable that the contact portion comprises more than three rolling members that are arranged around the exit opening to contact the surface of the skull, and a distal end of each rolling member is arranged on a virtual plane orthogonal to the optical axis. In order to lessen heat affection to the skull as much as possible at a time of laser emission and to cut the skull smoothly and quickly, a pulse laser is preferable.

Effect of the Invention

The present claimed invention is realized just by focusing attention on that the gap exists between the skull and the brain and the light interception board can be inserted into the gap. Since the laser travels just to a backside of the skull due to the light interception board, it is possible to cut the skull alone safely and securely without damaging the brain although a powerful laser is used. In addition, since the powerful laser like this can be used, it is also possible to shorten a time required for the craniotomy by speeding up the cutting rate.

In addition, it is possible to always keep an appropriate distance between the skull and the skull cutting device, namely, a distance wherein the focal point of the laser falls on the skull by means of the contact portion. Furthermore, operability is extremely superior because the body is connected through the optical fiber. As a result, it is possible to easily cut the skull along a cutting line with freedom. Furthermore, all the operator has to do is just form small holes on the skull at the beginning of the craniotomy and a substantial force is not required for the operator.

As mentioned above, in accordance with this invention, the operation itself can be simplified compared with a conventional operation. Furthermore, unlike the conventional operation there is no need of fixing the head of the patient with a strong force, thereby leading to reduction of burden also for the patient.

Furthermore, unlike the case of cutting the skull mechanically, since the cutting margin by the use of the laser is thin so that it is possible to coincide an outline of the bone flap with an opening outline of the skull from which the bone flap is cut as much as possible, it is possible to minimize a use of the fixing member in case of closing the opening of the skull by the bone flap.

EXPLANATION OF THE REFERENCE CODE

200 . . . laser oscillator
300 . . . optical fiber
400 . . . skull cutting device
1 . . . body
11 . . . main body
12 . . . head portion
1$a$ . . . exit opening
2 . . . contact portion
21 . . . rolling member
31 . . . support bar
32 . . . light interception board
4 . . . optical system
41 . . . circular polarizer
42 . . . collimator lens
43 . . . convex lens element
R . . . laser
P . . . skull
C . . . laser optical axis

BEST MODES OF EMBODYING THE INVENTION

One embodiment of the present claimed invention will be explained with reference to drawings.

First Embodiment

Figure 1:
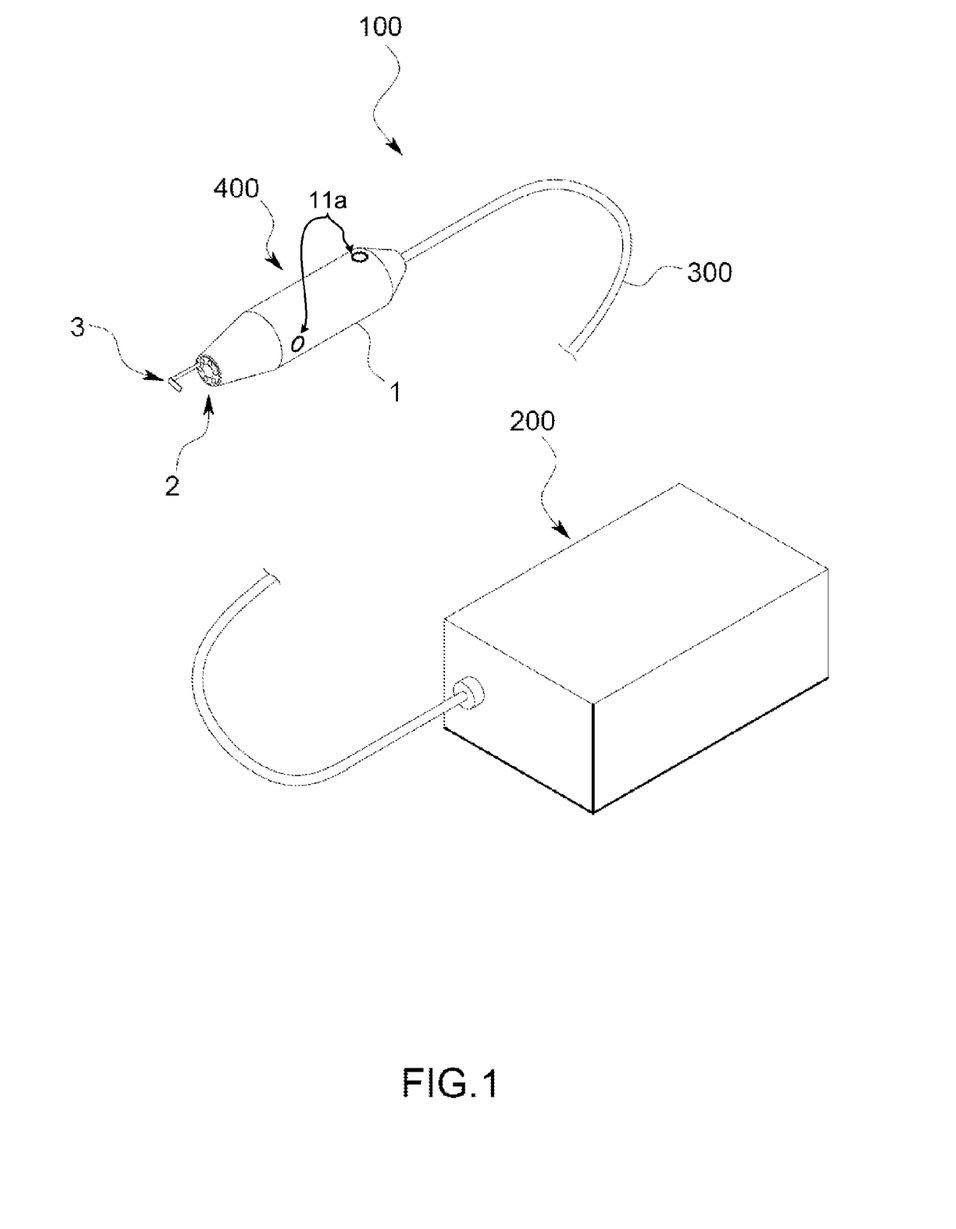
FIG. 1 is a schematic general view showing a craniotomy system in the first embodiment of this invention.

FIG. 1 schematically shows a craniotomy system 100 used for a brain surgery in accordance with this embodiment. In FIG. 1, a reference code 200 denotes a laser oscillator, a reference code 300 denotes an optical fiber that transmits the laser R output from the laser oscillator 200, and a reference code 400 denotes a skull cutting device 400 that cuts a skull P by making use of the laser R.

First, the laser oscillator 200 and the optical fiber 300 will be explained briefly. The laser oscillator 200 outputs, for example, the infrared ray pulse laser R (1.064 μm of wavelength, Nd: YAG) and its average power is 1 W through 20 W and its repetition frequency is about 0.1 kHz through 20 kHZ. The optical fiber 300 is flexible and uses, for example, a glass fiber.

Figure 2:
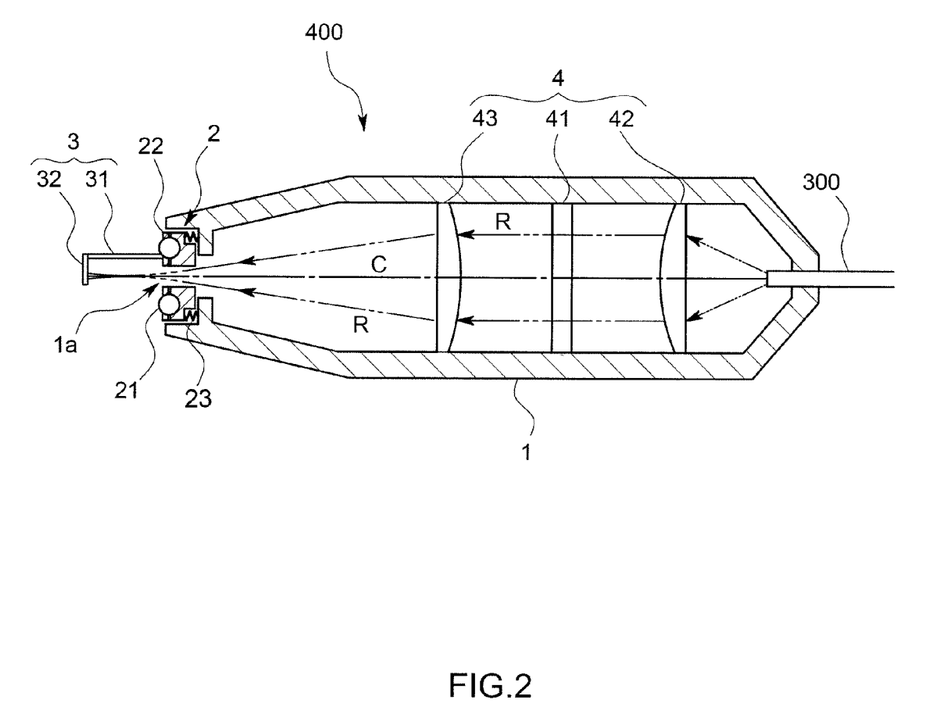
FIG. 2 is a schematic longitudinal end view showing an internal configuration of a skull cutting device in accordance with this embodiment.

Next, the skull cutting device 400 will be explained. The skull cutting device 400 comprises, as shown in FIG. 1 and FIG. 2, a body 1 that emits the laser R introduced from the laser oscillator 200 through the optical fiber 300 from an exit opening 1$a$ arranged at a distal end portion of the body 1, a contact portion 2 arranged in the body 1, and a limit mechanism 3 that limits a distance of emitting the laser R.

The body 1 is of a lengthy hollow shape and has a size and a weight suitable for a human to operate by grasping its side peripheral surface with one hand. A connection port is arranged at a proximal end portion of the body 1 to connect a distal end of the optical fiber 300, and the exit opening 1$a$ opens at a distal end portion of the body 1 to emit the laser R coming out from the distal end of the optical fiber 300 and passing through the inside of the body 1. In addition, arranged inside of the body 1 is the optical system 4 comprising a collimator lens 42 that parallelizes the laser R emitted from the optical fiber 300 in a diffused state, a circular polarizer 41 (λ/4 plate) that is intended to enlarge an excavation depth of the laser R and a convex lens 43 (fθ lens) that converges the laser R, each of which is arranged in series in this order from a laser injection side.

The contact portion 2 is arranged to project from a vicinity of the exit opening 1a, and a distance between a surface of the skull P and the exit opening 1a is so set that the optical axis C of the laser R is generally orthogonal to the surface of the skull P to be an area to which the laser R is emitted by making the contact portion 2 contact with the surface of the skull P in a predetermined mode to be described later and a focal point of the laser R falls on a center of a thickness of the skull P.

Figure 3:
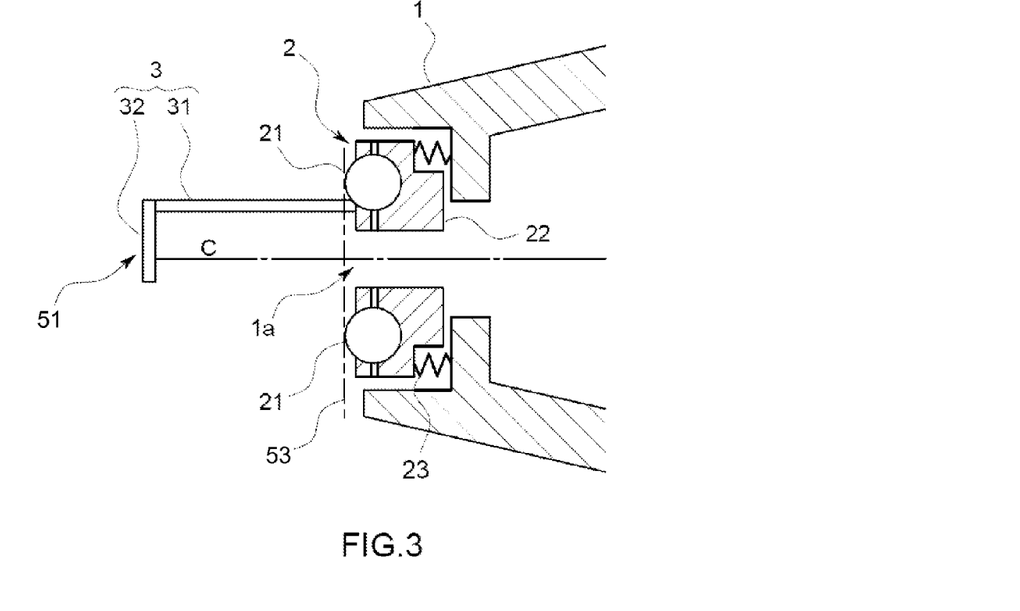
FIG. 3 is an enlarged partial end view showing a state that a contact portion in accordance with this embodiment is located at a natural position.
Figure 4:
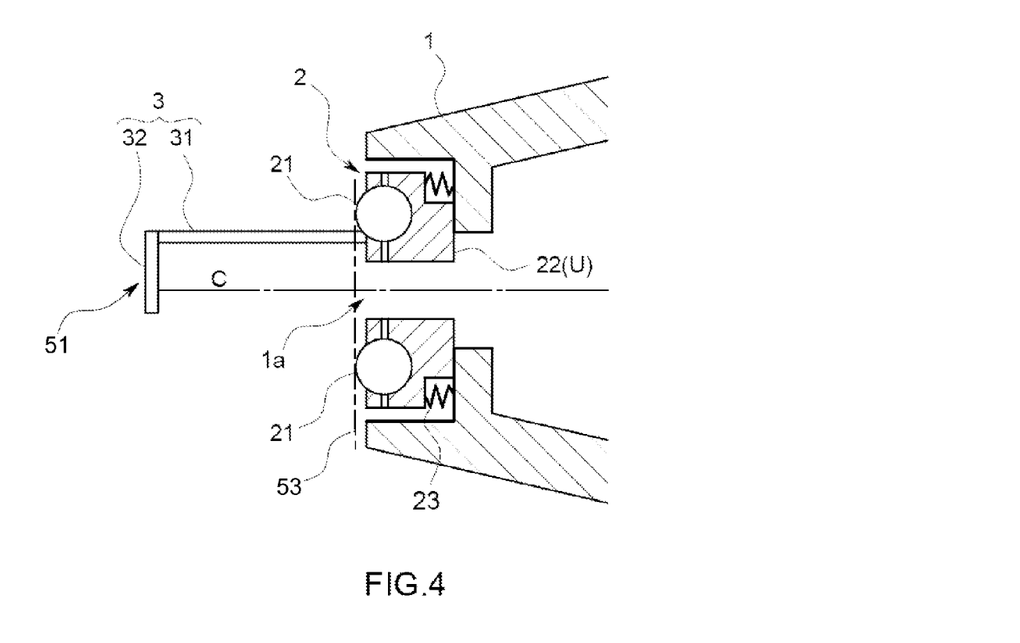
FIG. 4 is an enlarged partial end view showing a state that the contact portion in accordance with this embodiment is located at a reference position.

More concretely, as shown in FIG. 3 and FIG. 4, the contact portion 2 is radially arranged centering around the optical axis C of the laser R, and comprises more than three spherical rolling members 21 arranged so that a virtual plane 53 formed by connecting each distal end of the spherical rolling member 21 is orthogonal to the optical axis C of the laser R and a supporting member 22 that is mounted on a peripheral edge of the exit opening 1a and rotatably supports each of the spherical rolling members 21. The supporting member 22 is mounted on the body 1 through, for example, multiple elastic members 23 such as a plate spring so as to be slightly movable in a direction of the optical axis C. Furthermore, arranged in this embodiment is a detect device 51 such as a limit switch to detect that the supporting member 22 is located at a reference position U (refer to FIG. 4) as being a position where the supporting member 22 is pushed against the body 1 by an external force so that the supporting member 22 is unable to be further buried in the body 1.

The above-mentioned predetermined mode is a state wherein at least three rolling members 21 are pushed against the surface of the skull P and the supporting member 22 is located at the reference position U after the supporting member 22 is buried in the body 1 along the optical axis C. With this arrangement, the optical axis C of the laser R is generally orthogonal to the surface of the skull P and the distance between the surface of the skull P and the exit opening 1a becomes the predetermined distance determined in advance.

The control mechanism 3 comprises, as shown in FIG. 1 through FIG. 4, a support bar 31 of a predetermined length extending from the body 1 toward the emitting direction of the laser R while avoiding the optical path of the laser R, and a light interception board 32 that is arranged at a distal end of the support bar 31 and that blocks farther advance of the laser R. The support bar 31 extends in parallel to the optical axis C of the laser R from the peripheral portion of the exit opening 1a and a length of the support bar 31 is so set that the light interception board 32 arranged at the distal end of the support bar 31 is located between the back surface of the skull P and the brain. Since a thickness of the skull P varies between individuals, the length of the support bar 31 may be adjusted slightly. The light interception board 32 is a plate-shaped member positioned on the optical axis C of the laser R, and its size is set to be the same as a diameter of the laser R on the light interception board 32 or a little larger than the diameter of the laser R. In addition, the light interception board 32 is provided with, for example, a diffusion processing in order to diffuse the laser R on the surface of the light interception board 32.

Furthermore, in this embodiment, a safety mechanism is arranged to compulsorily halt emission of the laser R in a state except for the above-mentioned predetermined mode. This safety mechanism is not drawn in drawings, and may be configured by, for example, an electric circuit that receives an output signal of the detect device and halts the laser oscillator 200 in case of judging otherwise the predetermined mode from a content of the output signal.

Next, a method for operating the skull cutting device 400 having the above-mentioned arrangement will be explained.

Figure 5:
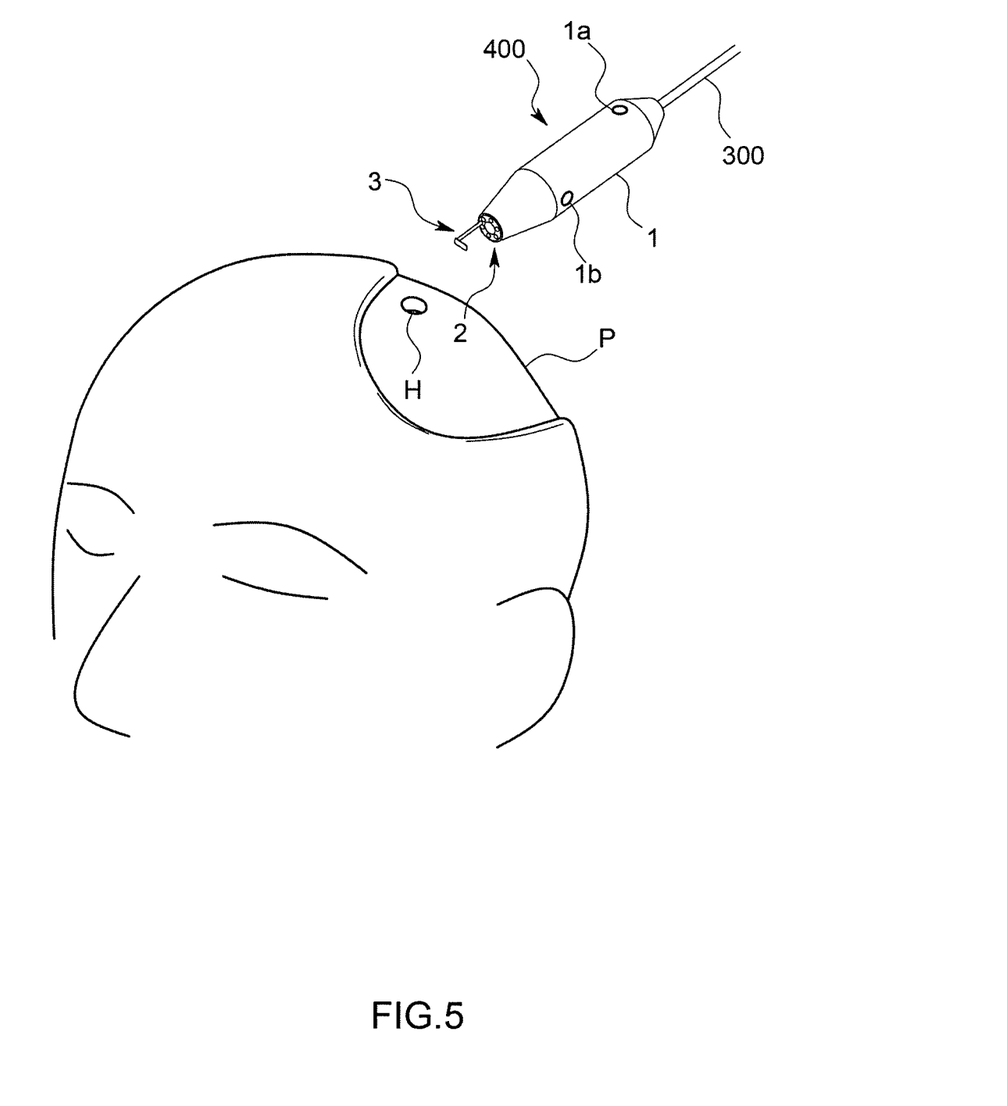
FIG. 5 is an explanatory view of an operation to show a case of conducting an operation by the use of the skull cutting device of this embodiment.

An operator first drills a quite small hole H whose diameter is a fraction of a conventional burr hole by the use of a drill at one portion of a range of the exposed skull P to which the craniotomy procedure is conducted (refer to FIG. 5). A size of the hole H may be so set that the support bar 31 and the light interception board 32 located at the distal end of the support bar 31 can be inserted thereinto. In this embodiment a diameter of the hole H is about 5 mm (conventionally, a plurality of bar holes of several cm diameter are drilled).

Figure 6:
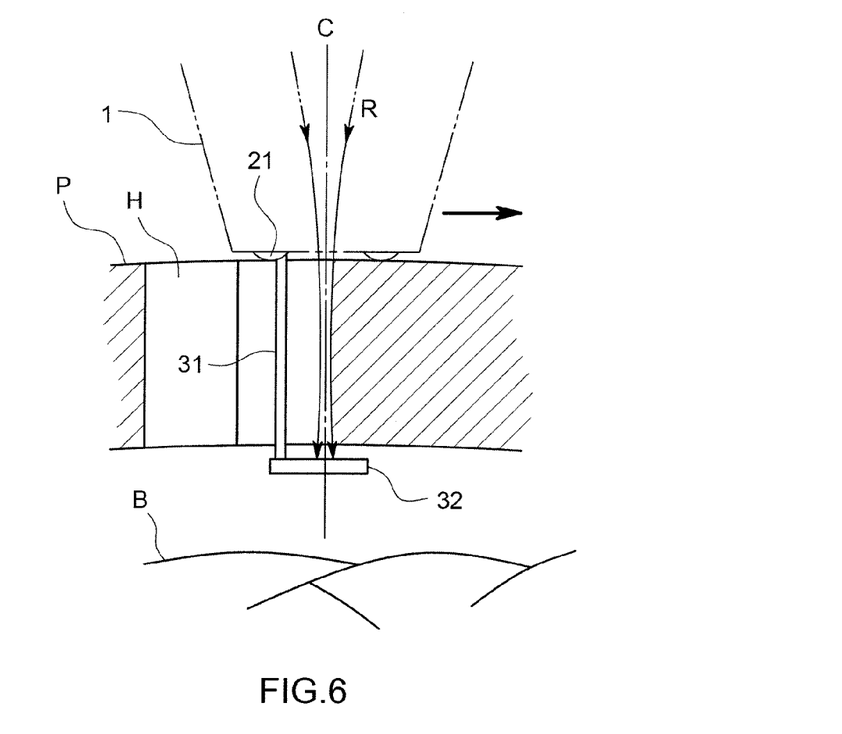
FIG. 6 is an explanatory view in section of the operation to show a state wherein a skull is cut by the use of the skull cutting device of this embodiment.

Next, the light interception board 32 and the support bar 31 are inserted into the hole H and the rolling members 21 are pushed against the surface of the skull P. When the body 1 is suitably pushed against the surface of the skull P so as to result in the predetermined mode, the detect device detects that the skull cutting device 400 is in the predetermined mode and, for example, a display lamp 11a arranged on the body 1 is lit. In the state shown in FIG. 6, the light interception board 32 is located in a gap between the back surface of the skull P and the surface of the brain B.

Figure 7:
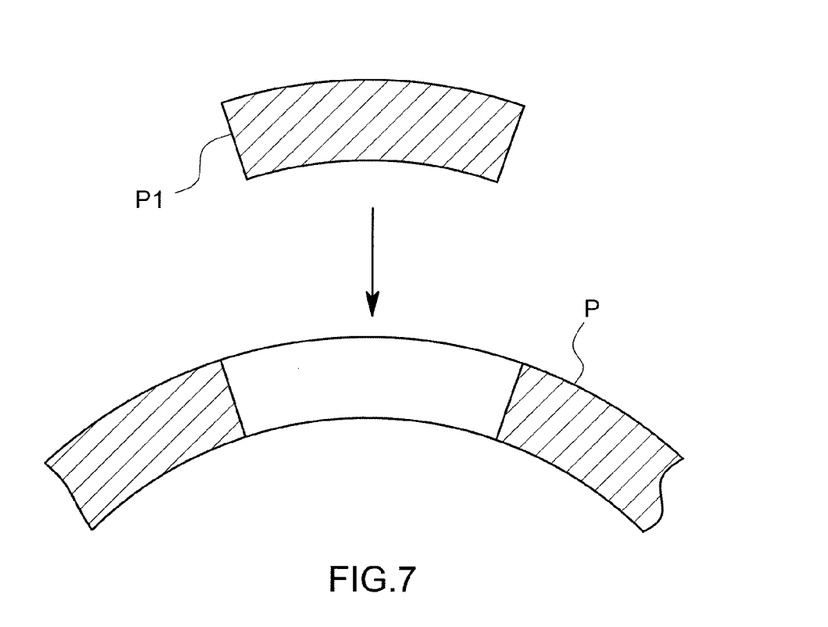
FIG. 7 is an explanatory view of the operation to show a case of returning a bone flap cut by the use of the skull cutting device of this embodiment.

When the operator verifies that the display lamp 11a is lit, the operator pushes a start switch 1b arranged on the body 1. With this operation, the laser R is emitted from the exit opening 1a and the laser R starts cutting the skull P. As mentioned, since the excavation depth of the laser R is deepened by the circular polarizer 41 so that the laser R travels across about a thickness (several cm) of the skull P without largely changing its diameter, as shown in FIG. 7, it is possible to thin down a cutting margin.

Then the skull P is cut by moving the body 1 along a predetermined cutting line with keeping the rolling members 21 pushed against the surface of the skull P.

With this arrangement, since the laser R travels only just to the backside of the skull P due to the light interception board 32 and the laser R never reaches the brain B, it is possible to secure the safety for the patient. In addition, since the safety mechanism is activated so that the laser R is not emitted in a state except for the above-mentioned predetermined mode, it is possible to avoid a case that, for example, the body 1 inclines so that the laser R reflects off the surface of the skull P and the laser R is emitted on the operator, thereby to secure the safety also for the operator.

Furthermore, since it is possible for the operator to cut the skull P smoothly and quickly by means of the laser R without applying a substantial force just by first forming small holes on the skull P, the operation itself can be simplified compared with a conventional operation. Furthermore, unlike the conventional operation, since there is no need to fix the head of the patient with a strong force, it is possible to lead to the reduction of burden also for the patient.

Since operability is extremely superior because the body 1 is connected through the optical fiber 300, this could be also one element to contribute to simplification of the operation. With this arrangement, it is possible to easily cut the skull P along the cutting line with freedom.

Furthermore, unlike the case of cutting the skull mechanically, the cutting margin by the use of the laser R is thin so that it is possible to coincide an outline of the bone flap P1 with an outline of the opening of the skull P from which the bone flap P1 is cut as much as possible and the cut surface is generally orthogonal to the surface of the skull P. As a result, if a spherical skull is cut as shown in FIG. 7, since a shape of the bone flap P1 becomes an inverted cone shape by itself, it is possible to return the bone flap P1 to the opening of the skull P so as to close the opening without caving in of the bone flap P1 and to minimize a use of the fixing member.

Second Embodiment

Figure 8:
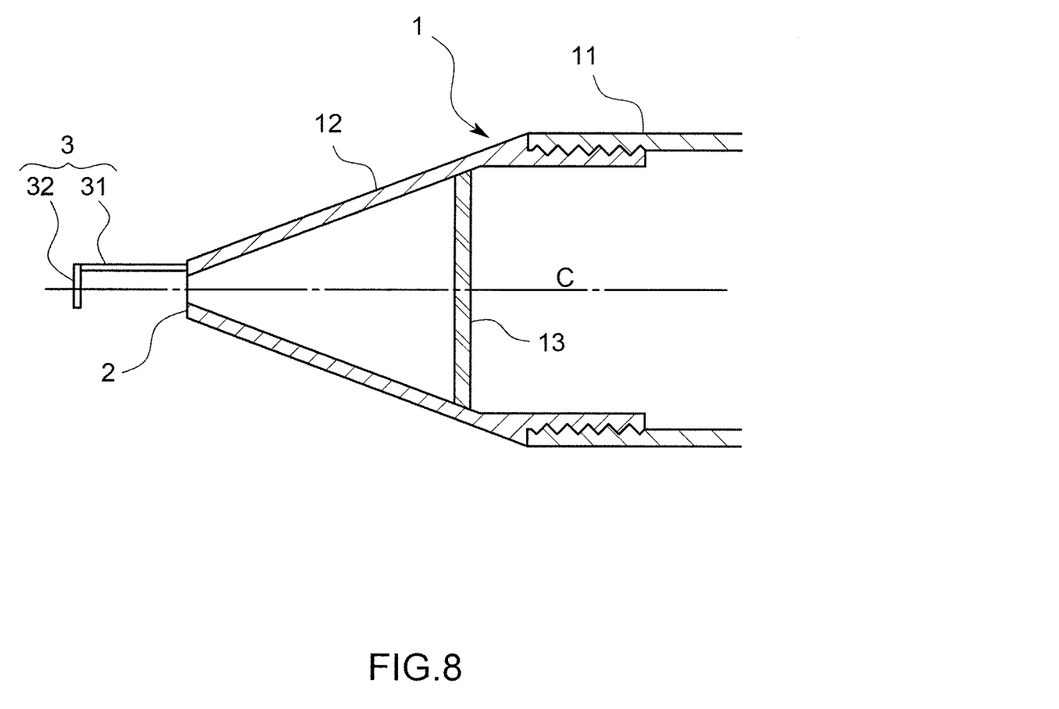
FIG. 8 is a schematic longitudinal end view partially showing an internal structure of a distal end of a skull cutting device in accordance with a second embodiment of this invention.

Next, the second embodiment of this invention will be explained with reference to FIG. 8. The same parts as those in the first embodiment are denoted by the same reference codes as those in the embodiment in principle.

In this embodiment, the body 1 comprises a main body 11 and a head portion 12 detachably arranged at a distal end of the main body 11.

The main body 11 is nontransparent and, for example, in a cylindrical shape and an optical system (not shown in FIG. 8) similar to that of the first embodiment is arranged inside of the main body 11.

The head portion 12 is threadably mounted on the distal end of the main body 11. The head portion 12 is in a hollow tapered shape with a laser exit opening 1a arranged at its distal end. The head portion 12 is made of a translucent material having a light diffusion action and forms a photic area as a whole.

In addition, inside of the head portion 12 a transparent antiscattering board 13 having an equal thickness is arranged orthogonal to the optical axis C of the laser R to divide the head portion 12.

In this embodiment, the distal end of the head portion 12 functions as the contact portion 2 and the detect device, not shown in drawings, such as a limit switch detects whether or not the contact portion 2 is pushed. More specifically, in the first embodiment, the detect device detects not only whether or not the contact portion 2 is pushed but also that the optical axis C and the body 1 are orthogonal to the surface of the skull P. However, in this embodiment the detect device does not detect that the body 1 is orthogonal to the surface of the skull P. Since a safety mechanism, not shown in drawings, works with the detect device, the safety mechanism does not interfere with emission of the laser R as far as the contact portion 2 is pushed.

With this arrangement, since the point on the skull P where the laser R is emitted can be checked with eyes through the photic area, it is possible to cut the skull P more accurately. In addition, since the photic area has a light diffusion action, a coherence effect of the laser R is lost so that it is possible to avoid a risk that might be caused in the case of checking with eyes.

Furthermore, the optical system can be protected from body fluid or a bone fragment scattering at a time of cutting the skull P by the antiscattering board 13. In addition, even though the head portion 12 is contaminated by the scattered body fluid or bone fragment, it is possible to dismount the head portion 12 alone from the main body 11, to thereby enhance the convenience.

In addition, in this embodiment, since the skull P can be cut at a free angle to a certain degree as far as the contact portion 2 makes contact with the skull P, it is also possible to make the bone flap P1 in a cone-shaped hollow shape by cutting the skull P with inclining the cutting surface to the surface of the skull P at a time of hollowing out, for example, a flat surface.

The present claimed invention is not limited to the above-mentioned embodiments. For example, this invention can be applied also to animals. The detect device is not only the mechanical device such as a limit switch but also an optical device or an electromagnetic device, or may be a device to detect proximity of the contact portion to an object (the skull).

In addition, the present claimed invention may be variously modified without departing from a spirit of this invention.

The invention claimed is:

1. A skull cutting device for cutting a skull by means of laser, comprising:
    a body that emits the laser introduced from a laser oscillator through an optical fiber from an exit opening, the exit opening arranged at a distal end thereof;
    a contact portion arranged at the distal end of the body to contact a surface of the skull, the contact portion comprising more than three rolling members arranged around the exit opening to contact the surface of the skull, and a distal end of each rolling member is arranged on a virtual plane orthogonal to the optical axis;
    a support bar extending from the body toward an emitting direction of the laser while avoiding an optical path of the laser, the support bar configured to penetrate the skull and extend to a back surface of the skull;
    a light interception board that is supported at a distal end of the support bar and that blocks farther advance of the laser by diffusing the laser boring through the skull when inserted between the back surface of the skull and a surface of the brain in a state that the contact portion makes contact with the surface of the skull; and
    a convex lens element converging the laser at a focal point between the virtual plane formed by the distal ends of the rolling members and the light interception board.

2. The skull cutting device described in claim 1, and further comprising a detect device that detects whether or not the contact portion makes contact with or is close to the surface of the skull.

3. The skull cutting device described in claim 2, wherein the detect device also detects whether or not an optical axis of the laser is generally orthogonal to the surface of the skull as being an area to which the laser is to be emitted.

4. The skull cutting device described in claim 1, wherein the support bar is of varying length.

5. The skull cutting device described in claim 1, and further comprising an optical system arranged inside of the body, wherein the optical system comprises a circular polarizer that circularly polarizes at least the laser emitted from the optical fiber and the convex lens element that converges the laser.

6. The skull cutting device described in claim 1, wherein the body comprises a main body, a head portion detachably arranged at a distal end of the main body and a transparent antiscattering plate of an even thickness that is arranged orthogonal to an optical axis of the laser and that divides an inside space of the head portion.

7. The skull cutting device described in claim 6, wherein the head portion is made of a translucent material having a light diffusion action and forms a photic area which is arranged near the exit opening of the body.

8. The skull cutting device described in claim 1, wherein the laser is a pulse laser.

9. A method for cutting a skull by means of laser, comprising:
    emitting from a body the laser introduced from a laser oscillator through an optical fiber from an exit opening, the exit opening arranged at a distal end thereof;
    contacting a surface of the skull with a contact portion arranged at the distal end of the body, the contact portion comprising more than three rolling members arranged around the exit opening to contact the surface of the skull, and a distal end of each rolling member is arranged on a virtual plane orthogonal to the optical axis;
    penetrating the skull and extending to a back surface of the skull with a support bar, the support bar extending from the body toward an emitting direction of the laser while avoiding an optical path of the laser; and
    blocking farther advance of the laser with a light interception board by diffusing the laser boring through the skull by inserting the light interception board between the back surface of the skull and a surface of the brain in a state that the contact portion makes contact with the surface of the skull, the light interception board supported at a distal end of the support bar;
    a convex lens element converging the laser at a focal point between the virtual plane formed by the distal ends of the rolling members and the light inception board.

* * * * *